United States Patent
Vaughan et al.

(10) Patent No.: US 11,007,015 B2
(45) Date of Patent: May 18, 2021

(54) APPARATUS AND METHOD FOR TRACKING A VOLUME IN A THREE-DIMENSIONAL SPACE

(71) Applicant: Queen's University at Kingston, Kingston (CA)

(72) Inventors: Thomas Vaughan, Ottawa (CA); Andras Lasso, Kingston (CA); Gabor Fichtinger, Kingston (CA); Tamas Ungi, Kingston (CA)

(73) Assignee: Queen's University at Kingston, Kingston (CA)

( * ) Notice: Subject to any disclaimer, the term of this patent is extended or adjusted under 35 U.S.C. 154(b) by 83 days.

(21) Appl. No.: 16/260,538

(22) Filed: Jan. 29, 2019

(65) Prior Publication Data
US 2019/0231441 A1   Aug. 1, 2019

Related U.S. Application Data

(60) Provisional application No. 62/623,082, filed on Jan. 29, 2018.

(51) Int. Cl.
| | |
|---|---|
| *A61B 34/20* | (2016.01) |
| *G06T 7/30* | (2017.01) |
| *G06T 7/70* | (2017.01) |
| *G06F 3/01* | (2006.01) |
| *A61B 34/10* | (2016.01) |
| *A61B 90/00* | (2016.01) |

(52) U.S. Cl.
CPC .............. *A61B 34/20* (2016.02); *G06F 3/017* (2013.01); *G06T 7/30* (2017.01); *G06T 7/70* (2017.01); *A61B 2034/105* (2016.02); *A61B 2034/2051* (2016.02); *A61B 2034/2055* (2016.02); *A61B 2090/378* (2016.02)

(58) Field of Classification Search
CPC .. G06T 7/30; G06T 7/33; G06T 7/337; G06T 7/70; G06T 7/73; G06T 7/74; G06T 2207/30204; A61B 34/20; A61B 2034/2051; A61B 2034/2055; A61B 2034/2065; A61B 2090/364; A61B 2090/367; A61B 2090/3983
See application file for complete search history.

(56) References Cited

U.S. PATENT DOCUMENTS

| | | | | |
|---|---|---|---|---|
| 5,394,875 A | * | 3/1995 | Lewis et al. | A61B 8/0833 128/916 |
| 6,973,202 B2 | * | 12/2005 | Mostafavi | A61B 6/463 382/103 |
| 8,081,815 B2 | * | 12/2011 | Kotake et al. | G06T 7/73 382/154 |
| 8,320,709 B2 | * | 11/2012 | Aratani et al. | G06T 7/74 382/291 |
| 9,734,589 B2 | * | 8/2017 | Yu et al. | G06T 7/292 |
| 2018/0104010 A1 | * | 4/2018 | Miga et al. | A61B 8/085 |

OTHER PUBLICATIONS

Ungi, T., et al., "Navigated breast tumour excision using electromagnetically tracked ultrasound and surgical instruments", IEEE Trans. Bio-Med. Eng. 63(3), 600-606 (2016).
Gauvin, G., et al., "Breast-Conserving Surgery using NaviKnife Technology: Pilot Study on Non-Palpable Tumours", Canadian Surgery Forum, Toronto, Ontario, Canada, Sep. 8-10, 2016 (Can. Surg. J. 2016, 59(4 Suppl. 1): S145-6).
Lasso, A., et al., "PLUS: open-source toolkit for ultrasound-guided intervention systems", IEEE Trans. Bio-Med. Eng. 61(10), 2527-2537 (2014).
Fedorov, A., et al., "3D Slicer as an image computing platform for the Quantitative Imaging Network", Magn. Reson. Imaging. 30(9), 1323-1341 (2012).

* cited by examiner

*Primary Examiner* — Andrew W Johns
(74) *Attorney, Agent, or Firm* — Stephen J. Scribner

(57) ABSTRACT

Provided are apparatus and methods for tracking a volume of interest in three dimensions in real time, using fewer than 6 DOF tracking information together with an external 6 DOE coordinate system. The apparatus and methods described herein provide more accurate, smaller, and less expensive tracking systems than prior approaches based on full 6 DOF tracking comprising translation and full orientation information. Embodiments may be used in applications such as surgical navigation, gaming, robotics, motion capture, and training.

21 Claims, 3 Drawing Sheets

APPARATUS AND METHOD FOR TRACKING A VOLUME IN A THREE-DIMENSIONAL SPACE

RELATED APPLICATION

This application claims the benefit of the filing date of Application No. 62/623,082, filed on 29 Jan. 2018, the contents of which are incorporated herein by reference in their entirety.

FIELD

This invention relates to apparatus, techniques, and methods that provide tracking of a volume of interest in a three-dimensional space in real time.

BACKGROUND

As accuracy of tracking of objects in three-dimensional (3D) space improves, techniques for implementing the technology in different fields are emerging. A technique [1, 2] based on electromagnetic (EM) tracking that has shown good performance in a surgical application for tracking a tissue volume of interest, such as a tumour, relies on two EM sensors, both reporting position and orientation in six degrees of freedom (6 DOF). According to this technique one 6 DOF sensor is located in or on the tissue volume of interest. In applications such as surgery, the 6 DOF sensor may be attached to a wire or needle that is inserted in the tissue volume of interest. The second 6 DOF sensor is a reference sensor located within the working space, typically on the patient in the vicinity of the surgical procedure.

Potential drawbacks of this technique include the wire or needle spinning in place within the tissue volume of interest, causing the 6 DOF sensor to spin with it, thus reporting inaccurate orientation of the tissue volume of interest. In addition, because a 6 DOF sensor is substantially large, it can be an obstacle in applications such as surgery, because it can obstruct the surgeon's hand motions in the working space, or the sensor may not fit inside the tissue volume of interest, or the sensor may obstruct the surgeon's view. Another drawback is that 6 DOF sensors are more expensive than, e.g., 5 DOF sensors, and there is greater computational complexity when processing the 6 DOF sensor position and orientation.

SUMMARY

One aspect of the invention relates to an apparatus for tracking a volume of interest, comprising: a tracking device that tracks at least two sensors in three dimensions, wherein the at least two sensors include: a reference sensor that provides a 6 DOF coordinate system in a working space and a marker sensor adapted to be attached to the volume of interest and to provide at least position of the volume of interest in at least 3 DOF; a tracking device that receives sensor data from the reference sensor and the marker sensor; a processor that receives data from the tracking device and outputs a change in position and/or orientation of the volume of interest within the working space in real time, according to the at least 3 DOF of the marker sensor within the 6 DOF coordinate system.

In one embodiment the marker sensor provides position and orientation of the volume of interest in 5 DOF. In another embodiment the marker sensor provides position and orientation of the volume of interest in 3 DOF.

According to embodiments, the change in position and/or orientation of the volume of interest within the working space in real time may be determined relative to an initial position and orientation of the volume of interest within the working space.

In one embodiment, the at least two sensors are wireless.
In one embodiment, the at least two sensors are electromagnetic (EM) or optical.
In one embodiment, the apparatus is part of a surgical or intervention navigation apparatus.
In one embodiment, the apparatus is part of a gaming apparatus, a robotic apparatus, a motion capture apparatus, or a training apparatus.
In one embodiment, the volume of interest is biological tissue.
In one embodiment, the apparatus is part of a surgical navigation apparatus, further comprising: a tool sensor adapted to be attached to a surgical tool and to provide position and orientation of the surgical tool; an imaging probe sensor adapted to be attached to an imaging probe of an imaging device and to provide position and orientation of the imaging probe; wherein the processor receives images from the imaging device, generates a three-dimensional delineation of the volume of interest from data points in the images, and three-dimensionally registers the volume of interest with the surgical tool; and an output device that displays the three-dimensionally registered volume of interest and the surgical tool in real time.
In one embodiment, the marker sensor is associated with a wire-localization needle.
In one embodiment, the volume of interest comprises a tumour.
In one embodiment, the working space comprises breast tissue.
In one embodiment, the surgical tool comprises a cutting tool, a cautery tool, a catheter, a needle, or a radiation therapy device.

Another aspect of the invention relates to programmed media for use with a processor, comprising: code stored on non-transitory storage media compatible with the processor, the code containing instructions to direct the processor to: communicate with a tracking device that tracks at least two sensors in three dimensions, wherein the at least two sensors include a reference sensor that provides a 6 DOF coordinate system in a working space, and a marker sensor adapted to be attached to the volume of interest and to provide at least position of the volume of interest in at least 3 DOF; wherein the processor outputs a change in position and/or orientation of the volume of interest within the working space in real time, according to the at least 3 DOF of the marker sensor relative to the 6 DOF coordinate system.

In one embodiment, the marker sensor provides position and orientation of the volume of interest in 5 DOF. In one embodiment, the marker sensor provides position and orientation of the volume of interest in 3 DOF.

In one embodiment, the change in position and/or orientation of the volume of interest within the working space in real time is determined relative to an initial position and orientation of the volume of interest within the working space.

Another aspect of the invention relates to a method for tracking a volume of interest, comprising: tracking at least two sensors in three dimensions, wherein the at least two sensors include: a reference sensor that provides a 6 DOF coordinate system in a working space, and a marker sensor adapted to be attached to the volume of interest and to provide at least position of the volume of interest in at least 3 DOF; outputting a change in position and/or orientation of the volume of interest within the working space in real time, according to the at least 3 DOF of the marker within the 6 DOF coordinate system.

In one embodiment of the method, the marker sensor provides position and orientation of the volume of interest in 5 DOF. In one embodiment of the method, the marker sensor provides position and orientation of the volume of interest in 3 DOF.

In one embodiment of the method, the change in position and/or orientation of the volume of interest within the working space in real time is determined relative to an initial position and orientation of the volume of interest within the working space.

In one embodiment of the method, the at least two sensors are electromagnetic (EM) or optical.

In one embodiment, the method is applied to surgical navigation or intervention.

In one embodiment, the method is applied to gaming, robotics, motion capture, or training.

In one embodiment of the method, the volume of interest is biological tissue.

In one embodiment, the method is applied to surgical navigation and further comprises: sensing position and orientation of a surgical tool within the 6 DOF coordinate system; sensing position and orientation of an imaging probe of an imaging device within the 6 DOF coordinate system; using a processor to receive images from the imaging device, generate a three-dimensional delineation of the volume of interest from data points in the images, and three-dimensionally register the volume of interest with the surgical tool; and display the three-dimensionally registered volume of interest and the surgical tool in real time on an output device.

In one embodiment of the method, the marker sensor is associated with a wire-localization needle.

In one embodiment of the method, the volume of interest comprises a tumour.

In one embodiment of the method, the working space comprises breast tissue.

In one embodiment of the method, the surgical tool comprises a cutting tool, a cautery tool, a catheter, a needle, or a radiation therapy device.

BRIEF DESCRIPTION OF THE DRAWINGS

For a greater understanding of the invention, and to show more clearly how it may be carried into effect, embodiments will be described, by way of example, with reference to the accompanying drawings, wherein.

DETAILED DESCRIPTION OF EMBODIMENTS

Figure 1A:
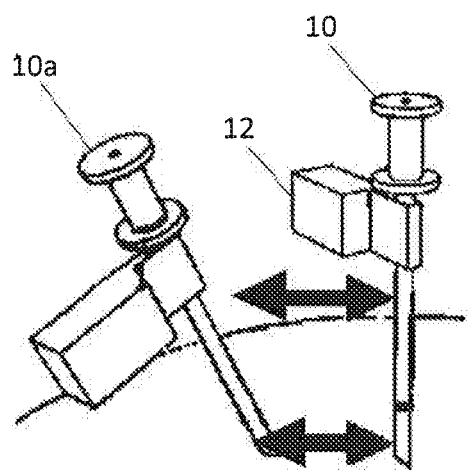
FIGS. 1A-1D are diagrams showing needle movements, including needle shift to and from the initial state, needle tilt, needle spin, needle in the initial state, respectively, according to embodiments described herein.

Embodiments described herein use real-time tracking to three-dimensionally delineate and track a volume of interest in a working space. Whereas embodiments are described primarily with respect to electromagnetic (EM) tracking, it will be appreciated that they may also be implemented using other sensing/tracking modalities, such as those based on optical tracking. Embodiments are described herein primarily with respect to surgical applications. However, it will be appreciated that the embodiments may be implemented for other applications, such as, but not limited to, gaming, motion capture, training, and robotics.

As used herein, the term "volume of interest" refers to an item, feature, object, etc., that is being tracked.

As used herein, the term "working space" refers to a three-dimensional space in which the volume of interest is being tracked.

Prior approaches (e.g., [1, 2]) as applied to surgery provide accurate EM 3D tracking of a tissue volume of interest. In breast cancer surgery, for example, this results in a significant reduction in the occurrence of positive margins during tumour resection. However, the prior tracking technique requires a 6 DOF sensor to track the volume of interest (i.e., the tumour). The large and expensive 6 DOF sensor may restrict hand motions in the surgical working space, and may capture and report inaccurate orientation information. Improving accuracy, reducing the size constraints, and reducing cost of the EM sensing system will ensure that the technique becomes adopted and widely used in patients. In particular, insofar as it may be desired that certain sensor configurations are disposable, such as when the sensors are configured with localization needles that are placed in tissue, the cost of using 6 DOF sensors may be prohibitive.

The apparatus and methods described herein provide more accurate, smaller, and less expensive tracking systems than prior apparatus or methods, by using fewer than 6 DOF to track the volume of interest within a 6 DOF coordinate system. For example, one embodiment uses only 5 DOF tracking of the volume of interest (a position and a three-dimensional vector) together with an external 6 DOF coordinate system, and provides superior performance relative to prior tracking methods based solely on full 6 DOF tracking information. Another embodiment uses only 3 DOF tracking of the volume of interest (i.e., position) together with an external 6 DOF coordinate system. Thus, it is demonstrated that full 6 DOF tracking (comprising translation and furl orientation information) is not required to capture all movements of a volume of interest.

Although the embodiments may be used to track position and orientation of any volume of interest, they are well-suited to tracking a volume that is mobile and/or deformable since the sensors allow estimation of the pose of the moving/deforming volume of interest. In one embodiment the apparatus includes a marker with a 5 DOF sensor, the marker adapted to be disposed in or on the volume of interest. In another embodiment the apparatus includes a marker with a 3 DOF sensor, the marker adapted to be disposed in or on the volume of interest. In various embodiments, the marker may comprise suitable hardware, such as pins, clips, needles, probes, and the like, so that it may be placed and anchored in or on the volume of interest. For example, where the volume of interest is a tissue volume, such as a tumour, the marker may comprise a localization needle. The localization needle may comprise one or more hooks or prongs to anchor it to the tissue volume of interest. In one embodiment, a 3 DOF sensor or a 5 DOF sensor is attached to the exterior of a localization needle. In another embodiment, a small 3 DOF sensor or 5 DOF sensor is embedded within the needle tip, which is in turn hooked into the tissue volume of interest.

Real-time tracking as described herein may be adapted for a variety of surgical procedures, minimally invasive interventions, and surgical navigation systems. Embodiments are particularly suitable for procedures in soft or deformable tissue, such as breast. For demonstrative purposes, embodiments relating to breast tumour resection will be described. It will be readily understood by those of ordinary skill in the art that the invention is not limited thereto, as embodiments may be applied to any organ, tissue, or structure, and corresponding procedure. Embodiments may also be applied to other procedures and interventions, such as, for example, radiation therapy interventions such as brachytherapy. In various embodiments and applications, one or more surgical tool is tracked in addition to the volume of interest. The surgical tool may be any tool or device as required by a procedure, e.g., a cutting tool, a cautery tool, a radiotherapy tool (e.g., a catheter, a linear accelerator, a needle, a device to deliver external beam radiation therapy, etc.). Accordingly, as used herein, the term "tool" or "surgical tool" is intended to refer to any tracked instrument, tool, or device that may be used or adapted for use with the apparatus and methods described herein for surgical and radiation therapy interventions.

A surgical navigation system including position and orientation tracking of a tissue volume of interest according to an embodiment described herein may employ an imaging modality based on ultrasound, computed tomography, magnetic resonance imaging, or projection imaging (e.g., X-ray), or a combination thereof. According to such embodiments, surgical navigation is provided by fusion of images obtained from an imaging modality in the same frame of reference as the tracked tissue volume of interest.

Results of preliminary trials in a surgical application (Example 3, below) using 5 DOF tumour tracking as described herein demonstrate a significant improvement in localization of the tumour during breast conserving surgery in patients. Thus, it is expected that embodiments may be incorporated into a surgical navigation system at reduced cost and complexity relative to prior 6 DOF approaches, while at the same time providing superior accuracy of tracking.

Embodiments will now be described in greater detail by way of the following non-limiting examples.

EXAMPLE 1

Data Transformations for a 5 DOF Marker Sensor

Figure 1B:
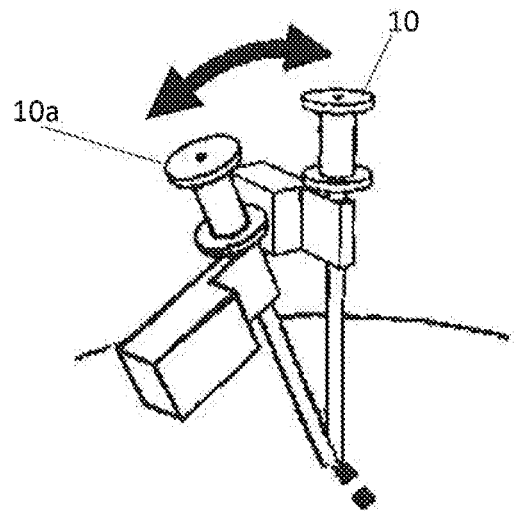
Figure 1C:
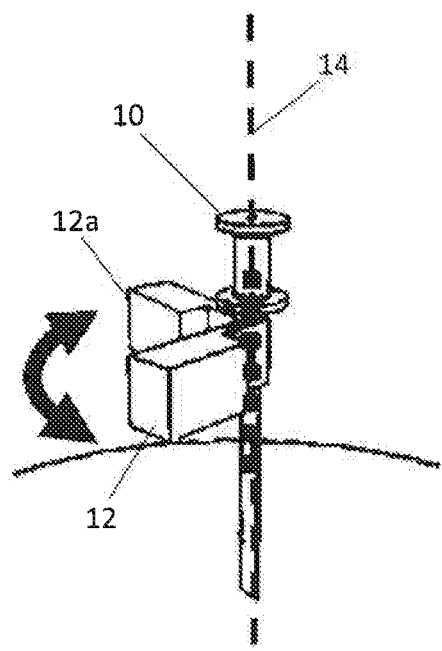

Data transformations used in the embodiments are described using biological tissue as an example of the volume of interest, with reference to FIGS. 1A-1D, which are diagrams showing needle movements, including needle shift to and from the initial state (FIG. 1A), needle tilt (FIG. 1B), needle spin (FIG. 1C), needle in an initial state (FIG. 1D), respectively. In the figures, a needle 10 with sensor 12 is shown in an initial state, dispose in a tissue volume. The arrows show the respective movement (shift, tilt, spin). In FIGS. 1A and 1B, movement of the needle 10 from an initial state is shown by the needle 10a. In FIG. 1C, rotation of the needle 10 from an initial state is shown by new position of the sensor 12a, as the needle 10 is rotated about the axis defined by dashed line 14.

Motions of the tissue volume of interest are restricted to two types: shift (FIG. 1A) and tilt (FIG. 1B). Tilt describes a specific type of rotation relative to an initial orientation and position (FIG. 1D) of the tissue volume of interest. Shift describes translation relative to the initial position of the tissue volume of interest. These motions are captured using 5 DOF tracking information (comprising position and a single orientation vector).

The initial position and orientation of the tissue volume of interest is recorded in 6 DOF after the sensor has been embedded or attached to the tissue volume of interest, but before the tissue volume of interest is operated on or manipulated. The initial position and orientation then stores the position and orientation of the tissue volume of interest before any external forces are applied (by e.g., cauterizing instruments, catheters, and so on). The 5 DOF tracking information comprises only position and an orientation vector.

Let the orientation vector represent the direction of a shaft (e.g., needle shaft, sensor shaft) which acts as one basis vector in three dimensions. Two arbitrary orthogonal base vectors are computed to give a total of three orthogonal basis vectors. These three basis vectors are computed relative to an external 6 DOF coordinate system (e.g., a tracker, a nearby 6 DOF sensor, or another instance of this invention).

Tilt and Shift are then computed continually from real time 5 DOF tracking information. In the following description, transformation matrices are indicated in bold beginning with a capital letter, three-dimensional vectors are indicated in bold beginning with a lower case letter, and scalar values are indicated in italics. Let Initial and Changed be two matrix transformations describing the position and orientation of the tissue volume of interest relative to a common coordinate system before and after moving, respectively. Let positionInitial represent the position of the tissue volume of interest before moving. Let positionChanged represent the position of the tissue volume of interest after moving. Let shaftInitial represent the orientation vector described by the 5 DOF tracking information before moving. Let shaftChanged represent the orientation vector described by the 5 DOF tracking information after moving. positionInitial, positionChanged, shaftInitial, shaftChanged are all given by the 5 DOF tracking information. Initial is already a frilly defined transformation matrix recorded as described above. The corresponding 6 DOF transformation matrix Changed is not yet folly defined, but it can be computed:

Changed=Shift*Tilt*Initial

Shift is modeled by a translation that is computed:
shiftTranslation=positionChanged−positionInitial Tilt is modeled as an axis-angle rotation, with axis passing through the origin of the Initial coordinate system. The axis direction and angle are computed:

$tiltAxis = |shaftInitial \times shaftChanged|$ $shaftsDotProduct = shaftInitial \cdot shaftChanged$ $shaftsAngleDifference = \mathrm{asin}(norm(shaftInitial \times shaftChanged))$ $tiltAngle = -180° - shaftsAngleDifference$ given $shaftsDotProduct < 0$ and -continued $shaftsAngleDifference < 0 = 180° - shaftsAngleDifference$ given $shaftsDotProduct < 0$ and $shaftsAngleDifference \geq 0 = shaftsAngleDifference$ otherwise

EXAMPLE 2

Data Transformations for a 3 DOF Marker Sensor

In this example, a 3 DOF (i.e., position-only) marker sensor is attached rigidly to a volume of interest and there is an external reference 6 DOF (position and full orientation sensor). Assuming there is no rotation, the volume of interest is tracked using an initial position and orientation, and shift.

This follows Example 1 regarding transformation matrices, three-dimensional vectors, and scalar values. Let Initial and Changed be two transformation matrices describing the position and orientation of the tissue volume of interest relative to a reference 6 DOF coordinate system before and after moving, respectively. Since the marker sensor only provides a position, there is no orientation information provided. The three orthogonal basis vectors that would normally describe orientation can be chosen arbitrarily.

Let markerPositionInitial be the position of the volume of interest before any movement happens, as measured by the marker sensor. Let markerPositionChanged be the position of the volume of interest after movement happens, as measured by the marker sensor. Let Shift be described using a translation vector as in Example 1.

shiftTranslation=markerPositionChanged−markerPositionInitial

Then:

Changed=Shift·Initial

EXAMPLE 3

Surgical Implementation

Background

Breast cancer is the most commonly diagnosed cancer in women worldwide. Early-stage breast cancer patients are preferably treated with breast conserving surgery (BCS). BCS is advantageous over mastectomy because of preserved cosmesis. BCS combined with radiotherapy has survival equivalent to mastectomy provided that no cancerous tissue is left inside the breast. However, if part of the tumour remains inside the breast then the local recurrence rate is significantly higher. A second or third excision, or a mastectomy, will be required in these cases. Available data indicate that 14% to over 50% of BCS patients will need re-excision.

Tumour Tracking

Needle localization is a standard technique used in BCS to mark the location of the tumour, i.e., the volume of interest. A needle or a hooked wire is implanted into the tumour under image guidance before surgery. A position and orientation sensor is fixed to the needle, and the tumour geometry is defined relative to the sensor. Throughout BCS, the tumour is moved together with the localization needle. The position and orientation sensor attached to the needle is used to capture the tumour movement. However, an important implication of this relationship is that needle movement is limited by the possible movements of the tumour.

Needle movement information was used to derive a system and method based on only 5 DOF tumour tracking. Three different types of needle movements are identified, relative to an initial state when the needle and tumour are not under external force from an instrument, an imaging probe, the surgeon's hands, the procedure, etc. The first type of needle movement is "shift", which is needle tip translation from the initial state (FIG. 1A). Since the needle tip is embedded in the tumour using a hook, shift provides crucial and reliable information for localizing the tumour. The second type of needle movement is "tilt", which is rotation of the needle that results in a change of needle shaft direction, relative to the initial state (FIG. 1B). It is rotation with axis perpendicular to the needle shaft and passing through the needle tip. The breast is a highly mobile organ, and during BCS it is reasonable to expect that the surgeon will need to lift or manipulate some of the tissue to cut deeper regions. Thus, tilt captures orientation of the tumour. The third type of needle movement is "spin", which is rotation of the needle around the needle shaft itself, relative to the initial state (FIG. 1C).

Figure 1D:
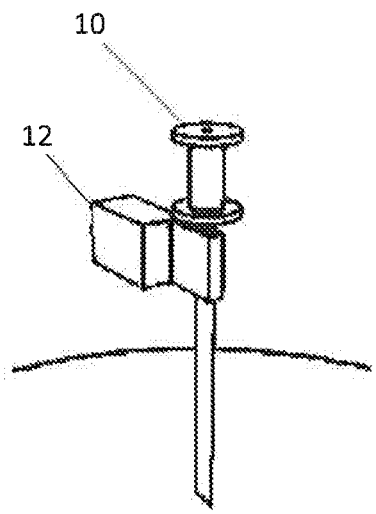

Together these three needle movements describe a transformation. However, it is recognized herein that since the tumour is embedded within the tissue, it cannot rotate around the needle shaft. If spin is detected, then it does not reflect true tumour movement. Such spin could occur if the sensor (whether inside or outside the needle) ever rotates around the shaft of the needle, or if there is sufficient torqueing force on the needle. Therefore, in accordance with embodiments described herein, needle shift and tilt provide sufficient information to describe the movement of the tumour from a known initial state (FIG. 1D). Thus, a 5 DOF tracking information was used to provide a needle shaft direction vector and a needle translation vector (as described in Example 1). The shall direction may be used to compute the tilt from the initial state. The translation is immediately taken as the needle shift. Therefore, 5 DOF tracking information provides all necessary information to fully describe the movement of the tumour from an established initial state. This represents a significant reduction in size and cost relative to prior approaches based on 6 DOF sensors.

Coordinate Systems

Figure 1E:
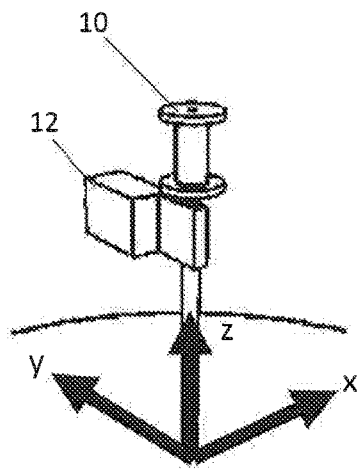
FIG. 1E is a diagram showing a needle coordinate system centered at the needle tip with z-axis parallel to the needle shaft, according to one embodiment.
Figure 2:
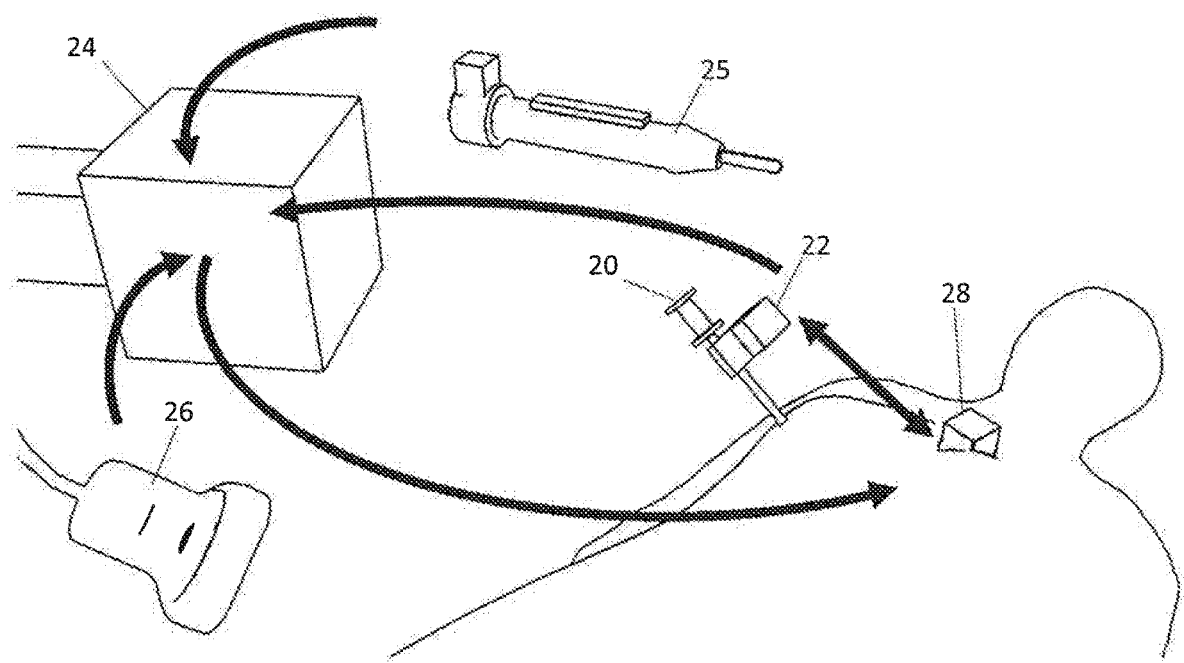
FIG. 2 is a diagram showing coordinate systems of a surgical tracking and navigation apparatus according to an embodiment of the invention, wherein arrows denote known transformations between coordinate systems.

Matrix transformations were used to represent all translations and rotations between coordinate systems. The coordinate systems are shown in FIG. 2. The Needle coordinate system measures the position and orientation of the needle, and is centered at the needle tip with z-axis parallel to the needle shaft, as shown in FIG. 1E. The tip and shaft can either be calibrated, or found on tracked ultrasound. The x- and y-axes do not have any distinct meaning, and can be chosen arbitrarily but still orthogonal to each other and to the z-axis. The Reference coordinate system measures the position and anatomical orientation of the patient, and is defined using a sensor secured to the patient. The ultrasound probe and surgical tool (e.g., electro-cauterizer) have coordinate systems and are tracked with their own dedicated sensors. An initial state is defined for the needle and used to compute the movements described above. The initial state is defined using the Initial coordinate system. A transformation matrix relative to the Reference coordinate system is recorded when there is no external force on the needle or on the tumour by, e.g., an ultrasound probe or surgical device. The Ultrasound and Cautery coordinate systems measure the positions of their respective tools.

Phantom Study

A proof-of-concept phantom study was conducted in which the described 5 DOF tracking was compared to a prior 6 DOF method. The phantom was made of soft plastic with a simulated tumour inside (cylindrical, 2 cm in length and 1 cm in diameter). The setup is shown diagrammatically in FIG. 2. The setup included the open-source software and resources described previously [1], a TrakStar™ system (Ascension Technology Corporation, Northern Digital Inc.), and followed the setup protocol for navigated BCS. Tracking data were collected using the open-source PLUS toolkit (www.plustoolkit.org) [3], and relayed to custom software on the 3D Slicer platform [4] using the OpenIGTLink protocol.

Referring to FIG. 2, an ultrasound machine (e.g., SonixGPS™ Tablet, Ultrasonix, Vancouver, Calif.) was used with an EM tracker 24 having multiple sensor ports. An ultrasound probe 26 with EM sensor and tracker broadcast data through the PLUS toolkit to the SlicerIGT navigation software running on the navigation computer, providing real-time registration and visualization of the tumour and tool 20 with EM sensor 22 (i.e., tool tip) position with respect to the reference sensor 28. The EM sensor 22 was attached to the localization needle 20 using a flexible clip, and was inserted into the tumour. The tracked cautery tool is shown at 25. The arrows show transformations between coordinate systems.

In order to make direct comparisons of the tracking methods, a single 6 DOF sensor was used to collect needle tracking data. The needle tip and shaft were calibrated on tracked ultrasound to create the Needle coordinate system. The 6 DOF tumour tracking method made use of the full transformation from the Needle coordinate system to the Reference, whereas the 5 DOF tumour tracking method made use of only the translation and needle shaft direction, as described above.

Tracked ultrasound was used to segment the simulated tumour and create a tumour shape model. The ground truth position and orientation of the tumour were accurately tracked by a sensor embedded in the tumour separate from the needle. The Initial coordinate system was established when there were no external forces on the phantom. Both 6 DOF- and 5 DOF-tracked tumour shape models were copies of the above tumour shape model.

Snapshots of transformations were recorded during various manipulations of the phantom tissue, such as making an incision and then simulating surgical forces on the phantom tissue and needle. The tumour ground truth was compared against the tumour as tracked by 6 DOF and described 5 DOF methods. The average Dice coefficient and Hausdorff distance were determined. The Dice coefficient represents the fraction of tumour that is tracked correctly. The Hausdorff distance represents the largest distance from the tracked boundary to the ground truth.

Results

It was observed that the 5 DOF method as described herein preserved shift and tilt of the needle, but not spin. This is desirable behaviour, since the tumour itself does not spin.

A total of 21 snapshots of the transformations were recorded. A summary of the results is provided in Table 1. Both metrics indicate that the 5 DOF tumour tracking method as described herein was superior to the 6 DOF method (p=0.002 for Dice coefficient and p<0.001 for Hausdorff distance, using one-tailed Wilcoxon signed rank tests). Based on observations and the reported metrics, it is concluded that the 5 DOF tumour tracking method performs better than the 6 DOF tumour tracking method. The improved performance of the 5 DOF tumour tracking method as described herein over the 6 DOF method is likely explained by the presence of needle spin. The average spin in the phantom experiment was 27.8 degrees. Advantageously, the benefits of 5 DOF tumour tracking as described herein may be achieved at lower cost and with less complexity than prior tracking/navigation systems based on 6 DOF tumour tracking.

TABLE 1

Average metrics (±stdev) reported for 6 DOF and 5 DOF tumour tracking methods.

| Tracking Method | Dice Coefficient | Hausdorff distance (mm) |
| --- | --- | --- |
| 6 DOF | 0.56 ± 0.18 | 8.8 ± 4.8 |
| 5 DOF | 0.71 ± 0.10 | 5.0 ± 1.9 |

To determine if the experiment was representative of actual surgery, clinical data were analyzed with the goal of quantifying needle spin. Ultrasound and tracking data were previously recorded in 17 BCS patient cases. The needle tip and shaft were segmented on the recorded ultrasound to create the Needle coordinate system. The Initial coordinate system was created from a snapshot of the Needle coordinate system immediately after the pre-surgical ultrasound scan. Samples of the tracking data were collected each second from the beginning of the ultrasound scan until the tumour was removed from the patient. On average, 1309 seconds (nearly 22 minutes) of samples were acquired for each patient. For each patient, the average needle spin was determined, and the 95th percentile spin was also determined to provide an indication of higher values of needle spin that occurred during surgery. The average needle spin was 30.4 degrees, which is in agreement with the needle spin (27.8 degrees) measured during the experiment.

Needle spin varied considerably from patient to patient. In seven patients, spin exceeded 30 degrees on average. Some of the 95th percentiles exceeded 90 degrees. It is unlikely that the tumour would have rotated by such large magnitudes inside the breast, even if the tumour was already partially detached. Thus, it is expected that 5 DOF tumour tracking as described herein will result in improved localization of the tumour during BCS in patients.

EXAMPLE 4

Volume Inaccuracy with 6 DOF Tracking

This example demonstrates a deficiency of 6 DOF tracking in breast cancer surgery. This example pertains to the volume outside the tissue volume of interest that could be erroneously tracked using 6 DOF tracking due to erroneous spin (as described above).

Figure 3A:
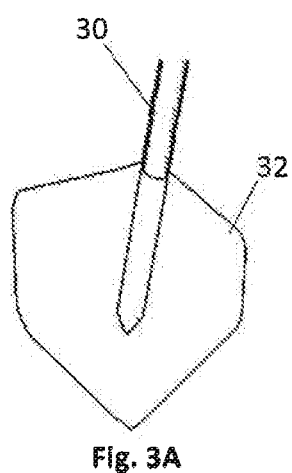
FIGS. 3A and 3B are diagrams showing tissue volume of interest and simulated volume resulting from marker spin, respectively, based on breast cancer patient data.
Figure 4A:
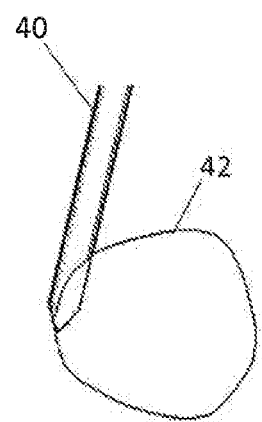
FIGS. 4A and 4B are diagrams showing tissue volume of interest and simulated volume resulting from marker spin, respectively, based on breast cancer patient data.
Figure 3B:
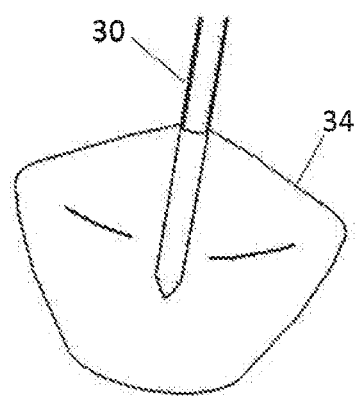
Figure 4B:
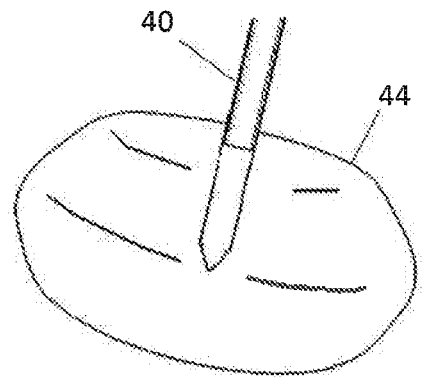

A simulation was performed using clinical data of tissue volumes of interest and marker placements for 17 breast cancer patient cases. Spin was calculated around the marker to simulate erroneous rotational data. A union was computed from resulting spun volumes to measure the total amount of extra volume that could be erroneously tracked. FIGS. 3A-3B and 4A-4B show two examples, in which FIGS. 3A and 4A show tissue volumes of interest 32, 42 with shafts of inserted markers 30, 40 for two patients. In FIGS. 3B and 4B, the corresponding unions of spun volumes 34, 44 are shown. It is appreciated that the unions of spun volumes, representing the volumes that could be tracked if spin is not corrected, are larger than the volumes of interest. For the 17 patients, the average tissue volume of interest was 2,080 cubic millimeters, and the average union volume was 7,010 cubic millimeters. This represents more than a threefold increase in tracked volume compared to the average tissue volume of interest. Thus, accuracy of the procedure may be significantly improved if spin is corrected as described herein.

All cited publications are incorporated herein by reference in their entirety.

Equivalents

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

[1] Ungi, T., Gauvin, G., Lasso, A., Yeo, C. T., Pezeshki, P., Vaughan, T., Carter, K., Rudan, J., Engel, C. J. and Fichtinger, G.: Navigated breast tumour excision using electromagnetically tracked ultrasound and surgical instruments. IEEE Trans. Bio-Med. Eng. 63(3), 600-606 (2016).

[2] Gauvin, G., Ungi, T., Lasso, A., Yeo, C. T., Fichtinger, G., Jabs, D., Walker, R., Merchant, S., Rudan, J., Engel C. J.: Breast-Conserving Surgery using NaviKnife Technology: Pilot Study on Non-Palpable Tumours. Canadian Surgery Forum, Toronto, Ontario, Canada, Sep. 8-10, 2016. (Can. Surg. J. 2016, 59(4 Suppl. 1): S145-6).

[3] Lasso, A., Heffter, T., Rankin, A., Pinter, C., Ungi, T. and Fichtinger, G.: PLUS: open-source toolkit for ultrasound-guided intervention systems. IEEE Trans. Bio-Med. Eng. 61(10), 2527-2537 (2014).

[4] Fedorov, A., Beichel, R., Kalpathy-Cramer, Finet, J., Fillion-Robin, J. C., Pujol, S., Bauer, C., Jennings, D., Fennessy, F., Sonka, M. and Buatti, J.: 3D Slicer as an image computing platform for the Quantitative Imaging Network. Magn. Reson. Imaging, 30(9), 1323-1341 (2012).

The invention claimed is:

1. An apparatus for tracking a volume of interest, comprising:
a tracking device that receives signals from at least two sensors in three dimensions and outputs tracking data, wherein the at least two sensors include:
a reference sensor that provides a 6 DOF coordinate system in a working space;
a marker sensor adapted to be attached to the volume of interest and to provide position of the volume of interest in 3 DOF;
a processor that receives tracking data from the tracking device and uses the tracking data to determine a first matrix transformation describing a position of the volume of interest before it is moved and a second matrix transformation describing the position of the volume of interest after it is moved, relative to a common coordinate system; and
resolves the first and second matrix transformations to output a change in position of the volume of interest within the working space in real time, according to the 3 DOF of the marker sensor within the 6 DOF coordinate system.

2. The apparatus of claim 1, wherein the marker sensor provides position and orientation of the volume of interest; and
the processor uses the tracking data to determine a first matrix transformation describing the position and orientation of the volume of interest before it is moved and a second matrix transformation describing the position and orientation of the volume of interest after it is moved, relative to a common coordinate system; and
resolves the first and second matrix transformations to output a change in position and/or orientation of the volume of interest within the working space in real time in 5 DOF within the 6 DOF coordinate system.

3. The apparatus of claim 2, wherein the change in position and/or orientation-of the volume of interest within the working space in real time is determined relative to an initial position and orientation of the volume of interest within the working space.

4. The apparatus of claim 1, wherein the apparatus is part of a surgical or intervention navigation apparatus, gaming apparatus, robotic apparatus, motion capture apparatus, or training apparatus.

5. The apparatus of claim 1, wherein the apparatus is part of a surgical navigation apparatus, further comprising:
a tool sensor adapted to be attached to a surgical tool and to provide position and orientation of the surgical tool;
an imaging probe sensor adapted to be attached to an imaging probe of an imaging device and to provide position and orientation of the imaging probe;
wherein the processor receives images from the imaging device, generates a three-dimensional delineation of the volume of interest from data points in the images, and three-dimensionally registers the volume of interest with the surgical tool; and
an output device that displays the three-dimensionally registered volume of interest and the surgical tool in real time.

6. The apparatus of claim 5, wherein the marker sensor is associated with a wire-localization needle.

7. The apparatus of claim 5, wherein the volume of interest comprises a tumour.

8. The apparatus of claim 5, wherein the working space comprises breast tissue.

9. The apparatus of claim 5, wherein the surgical tool comprises a cutting tool, a cautery tool, a catheter, a needle, or a radiation therapy device.

10. Programmed media for use with a processor, comprising:
code stored on non-transitory storage media compatible with the processor, the code containing instructions to direct the processor to:
communicate with a tracking device that receives signals from at least two sensors in three dimensions and outputs tracking data, wherein the at least two sensors include:
a reference sensor that provides a 6 DOF coordinate system in a working space;
a marker sensor adapted to be attached to the volume of interest and to provide position of the volume of interest in 3 DOF;
wherein the processor receives the tracking data from the tracking device and uses the tracking data to determine a first matrix transformation describing the position of the volume of interest before it is moved and a second matrix transformation describing the position of the volume of interest after it is moved, relative to a common coordinate system; and resolves the first and second matrix transformations to output a change in position of the volume of interest within the working space in real time, according to the 3 DOF of the marker sensor relative to the 6 DOF coordinate system.

11. The programmed media of claim 10, wherein the marker sensor provides position and orientation of the volume of interest; and the processor uses the tracking data to determine a first matrix transformation describing the position and orientation of the volume of interest before it is moved and a second matrix transformation describing the position and orientation of the volume of interest after it is moved, relative to a common coordinate system; and resolves the first and second matrix transformations to output a change in position and/or orientation of the volume of interest within the working space in real time in 5 DOF within the 6 DOF coordinate system.

12. The programmed media of claim 11, wherein the change in position and/or orientation of the volume of interest within the working space in real time is determined relative to an initial position and orientation of the volume of interest within the working space.

13. A method for tracking a volume of interest, comprising:

using a tracking device to receive signals from at least two sensors in three dimensions and output tracking data, wherein the at least two sensors include:
 a reference sensor that provides a 6 DOF coordinate system in a working space;
 a marker sensor adapted to be attached to the volume of interest and to provide position of the volume of interest in 3 DOF;

using the tracking data to determine a first matrix transformation describing the position of the volume of interest before it is moved and a second matrix transformation describing the position of the volume of interest after it is moved, relative to a common coordinate system; and resolving the first and second matrix transformations and outputting a change in position of the volume of interest within the working space in real time, according to the 3 DOF of the marker within the 6 DOF coordinate system.

14. The method of claim 13, wherein the marker sensor provides position and orientation of the volume of interest;
 wherein the tracking data is used to determine a first matrix transformation describing the position and orientation of the volume of interest before it is moved and a second matrix transformation describing the position and orientation of the volume of interest after it is moved, relative to a common coordinate system; and
 the first and second matrix transformations are resolved to output a change in position and/or orientation of the volume of interest within the working space in real time in 5 DOF within the 6 DOF coordinate system.

15. The method of claim 14, wherein the change in position and/or orientation of the volume of interest within the working space in real time is determined relative to an initial position and orientation of the volume of interest within the working space.

16. The method of claim 14, applied to surgical navigation, further comprising:
 sensing position and orientation of a surgical tool within the 6 DOF coordinate system;
 sensing position and orientation of an imaging probe of an imaging device within the 6 DOF coordinate system;
 using a processor to receive images from the imaging device, generate a three-dimensional delineation of the volume of interest from data points in the images, and three-dimensionally register the volume of interest with the surgical tool; and
 display the three-dimensionally registered volume of interest and the surgical tool in real time on an output device.

17. The method of claim 16, wherein the marker sensor is associated with a wire-localization needle.

18. The method of claim 16, wherein the volume of interest comprises a tumour.

19. The method of claim 16, wherein the working space comprises breast tissue.

20. The method of claim 16, wherein the surgical tool comprises a cutting tool, a cautery tool, a catheter, a needle, or a radiation therapy device.

21. The method of claim 13, applied to surgical navigation or intervention, gaming, robotics, motion capture, or training.

* * * * *